United States Patent

Sawa et al.

[11] Patent Number: 4,579,946
[45] Date of Patent: Apr. 1, 1986

[54] PROCESS FOR SYNTHESIS OF 2-VINYL-4,6-DIAMINO-S-TRIAZINE

[75] Inventors: Natsuo Sawa, Nakatado; Takeshi Masuda, Marugame, both of Japan

[73] Assignee: Shikoku Chemicals Corporation, Kagawa, Japan

[21] Appl. No.: 690,248

[22] Filed: Jan. 10, 1985

[51] Int. Cl.$^4$ .................................... C07D 251/18
[52] U.S. Cl. .................................... 544/205
[58] Field of Search ........................ 544/205

[56] References Cited

U.S. PATENT DOCUMENTS

| | | | |
|---|---|---|---|
| 2,689,238 | 9/1954 | Thomas | 544/205 |
| 2,726,229 | 12/1955 | Padbury et al. | 544/205 |
| 3,637,689 | 1/1972 | Inoue et al. | 544/205 |
| 4,189,577 | 2/1980 | Sawa et al. | 544/222 |

FOREIGN PATENT DOCUMENTS 60-19772  1/1985  Japan .

Primary Examiner—John M. Ford
Attorney, Agent, or Firm—Sherman and Shalloway

[57] ABSTRACT

Disclosed is a process for the synthesis of 2-vinyl-4,6-diamino-S-triazine having the following structural formula:

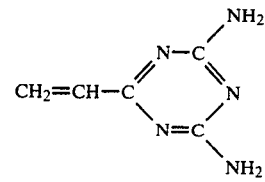

which comprises heating an imidazolyl-S-triazine compound represented by the following general formula:

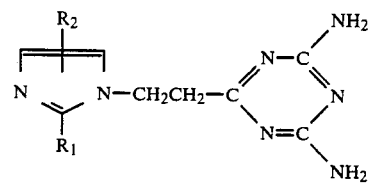

wherein $R_1$ stands for a hydrogen atom, a methyl group or an ethyl group, and $R_2$ stands for a hydrogen atom or a methyl group, or an isocyanuric acid-addition product thereof under reduced pressure in the presence of a polymerization inhibitor.

According to this process, 2-vinyl-4,6-diamino-S-triazine can be manufactured at a low cost on an industrial scale.

10 Claims, No Drawings

PROCESS FOR SYNTHESIS OF 2-VINYL-4,6-DIAMINO-S-TRIAZINE

BACKGROUND OF THE INVENTION

(1) Field of the Invention

The present invention relates to a process for the synthesis of 2-vinyl-4,6-diamino-S-triazine (hereinafter referred to as "VT"). More particularly, the present invention provides a process for preparing VT in large quantities at low costs.

(2) Description of the Prior Art

VT is a compound which is valuable as a comonomer, and it is known that if a diamino-S-triazine is introduced into side chains of a polymer, the softening point and glass transition point of the polymer are greatly elevated as compared with those of the non-modified polymer, and the specific gravity is increased and the solubility is prominently changed (see, for example, Nadao and Kakurai: Collection of Polymer Theses, 32, 308 (1975) and T. Seo, K. Abe, H. Honma and T. Kakurai: Polym. Prepn., 20, 661 (1979)).

Several processes as described below are known for the synthesis of VT. Namely, there can be mentioned a process in which biguanide is reacted with acrylic acid chloride (C. G. Overberger et al: J.A.C.S., 80, 988 (1958)), a process in which dicyandiamide is reacted with β-dimethylaminopropionitrile (French Pat. No. 1,563,255 (1967) to Hoechst AG), a process in which 1,2-di(4,6-diamino-S-triazinyl-(2))-cyclobutane is heated at 320° C. under reduced pressure (Japanese Patent Publication No. 35068/71 to Asahi Kasei), and a process in which 2-β-methoxyethyl-4,6-diamino-S-triazine is heated at 350° C. in a nitrogen current (Suddeutsche Kalkstickstoff Werke A.G.: Offen. 2, 135, 881 (1973)).

However, these known processes are defective in that the starting materials are expensive or the reaction procedures are complicated. Accordingly, none of these known processes are suitable for industrial working.

SUMMARY OF THE INVENTION

It is therefore a primary object of the present invention to provide a process for synthesizing VT in large quantities at low costs, which is suitable for industrial working.

More specifically, in accordance with the present invention, there is provided a process for the synthesis of 2-vinyl-4,6-diamino-S-triazine having the following structural formula:

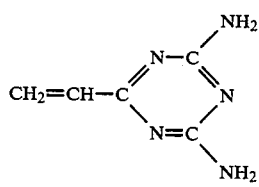

which comprises heating an imidazolyl-S-triazine compound represented by the following formula:

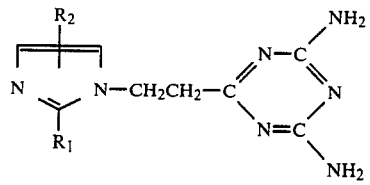

wherein $R_1$ stands for a hydrogen atom, a methyl group or an ethyl group, and $R_2$ stands for a hydrogen atom or a methyl group, or an isocyanuric acid-addition product thereof under reduced pressure in the presence of a polymerization inhibitor.

DETAILED DESCRIPTION OF THE INVENTION

The process of the present invention can be expressed by the following reaction formula:

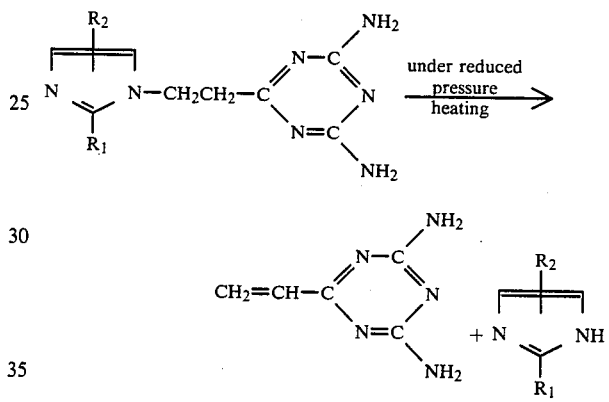

wherein $R_1$ and $R_2$ are as defined above, or

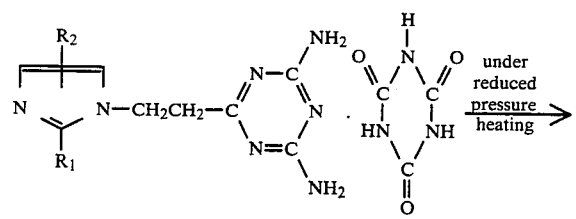

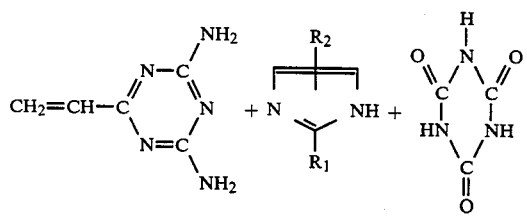

wherein $R_1$ and $R_2$ are as defined above.

The starting imidazolyl-S-triazine compound used in the process of the present invention is easily obtained from acrylonitrile, an imidazole compound and dicyandiamide according to the process disclosed in Japanese Patent Publication No. 36391/72.

An isocyanuric acid-addition product of the imidazolyl-S-triazine compound is easily obtained by reacting an imidazolyl-S-triazine compound with isocyanuric acid according to the process disclosed in U.S. Pat. No. 4,205,156.

The yield in the reaction of forming the imidazolyl-S-triazine compound or its isocyanuric acid-addition product from the imidazole compound is very good, and the operation procedures for forming VT from this starting substance are very simple and the yield is very good, which will readily be understood from Examples given hereinafter. Accordingly, the reaction of the present invention is very suitable for working on an industrial scale.

Embodiments of the reaction of the present invention will now be described in detail.

The starting imidazolyl-S-triazine compound is heated at a temperature of 180° to 320° C. under a reduced pressure of about 5 to about 20 mmHg for an appropriate time in the presence of an appropriate polymerization inhibitor in an appropriate reaction vessel in which a reduced pressure as described above can be maintained. By this heating, VT and the imidazole compound are sublimated to adhere to the wall of the upper portion of the reaction vessel. It is preferred that the wall of the upper portion of the reaction vessel be air-cooled or water-cooled.

The adhering reaction product is collected and washed with water to remove the imidazole compound, and the residue is recrystallized from water to obtain intended VT.

When the isocyanuric acid-addition adduct of the imidazolyl-S-triazine compound is used, the adduct is heated at 180° to 320° C. under a reduced pressure of about 5 to about 20 mmHg for an appropriate time in the presence of an appropriate polymerization inhibitor in an appropriate reaction vessel in which a reduced pressure as described above can be maintained. VT and the imidazole compound are sublimated to adhere to the wall of the upper portion of the reaction vessel. It is preferred that the wall of the upper portion of the reaction vessel be air-cooled or water-cooled.

A higher degree of the pressure reduction is preferred, but about 5 mmHg is sufficient. The reaction time is within one hour.

The adhering reaction product is washed with water to remove the imidazole compound and isocyanuric acid. The residue is recrystallized from water to obtain intended VT.

As typical examples of the polymerization inhibitor to be used in the present invention, there can be mentioned sodium sulfide, potassium sulfide, hydroquinone, copper sulfate and $\beta$-naphthylamine. Among these compounds, sodium sulfide gives a highest polymerization-inhibiting effect.

In carrying out the process of the present invention, a powdery or granular heat-conducting medium may be present in the reaction system so as to increase the heat conductivity in the reaction system. As typical instances of the powdery or granular heat-conducting medium to be used in the present invention, there can be mentioned quartz sand, sea sand, river sand, glass powder, silica powder, alumina powder, iron powder, copper powder, brass powder, bronze powder, aluminum powder and zinc powder. It is preferred that the size of the powdery or granular heat-conducting medium be in the range of 32 to 7 mesh according to the Tyler standard. It also is preferred that the powdery or granular heat-conducting medium be mixed with the starting substance so that the amount of the medium is larger than the amount of the starting substance based on the weight, and the reaction be then carried out.

The properties of VT are now described.

Melting Point: 239° to 241° C.
Solubility Characteristics:
Soluble in hot water and difficulty soluble in hot methanol, hot ethanol and hot acetone.
Basicity: Substantially neutral.
Polymerizability: A polymer insoluble in hot water is obtained when VT is dissolved in hot water and azobisisobutyronitrile is added to the solution.
TLC (alumina, silica and EtOH): Rf=0.0.
$v_{cm^{-1}}{}^{KBr}$: 3340, 3170, 1680 (fourth absorption), 1655 (second absorption), 1550 (first absorption), 1460 (fifth absorption), 1425 (third absorption), 1370, 1265, 1130, 985, 960, 835 (sixth absorption)
NMR ($d_6$-DMSO), $\delta$: 6.76 (multiplet, 4H), 6.35–6.45 (triplet, 2H), 5.59–5.72 (quadruplet, 1H)
Elementary Analysis Values: C=44.28%, H=5.07%, N=50.52%.

The present invention will now be described in detail with reference to the following Examples that by no means limit the scope of the invention.

EXAMPLE 1

In 7 ml of water were dissolved 20.5 g (0.1 mole) of a crystal of 2-($\beta$-imidazolyl-1')-ethyl-4,6-diamino-S-triazine and 2.2 g (0.008 mole) of Na$_2$S.9H$_2$O, and the aqueous solution was sufficiently mixed and dried and solidified under reduced pressure to obtain a starting material. This operation was performed so that the polymerization inhibitor was uniformly stuck to the crystal of the imidazolyl-S-triazine compound.

The so-obtained starting material and 25 g of quartz sand (having a size of 16 Tyler mesh) were charged in a Claisen flask having a side arm and an inner capacity of about 100 ml, and the bottom portion of the flask was wrapped with a hood on an electric heater and heating was carried out under a reduced pressure of 3 mmHg. Thus, the iner tempeature of the flask was maitaiend at 250° C. for 0.5 hour. After natural cooling, the sublimation product adhering to the inner wall of the upper portion and side arm of the flask was collected, and 36 ml of water was added to the collected sublimation product and the mixture was stirred at room temperature for a while. The insoluble substance (crude VT) was recovered by filtration and recrystallized from 100 mm of water to obtain 8.5 g (the yield being 62%) of intended VT characterized by a melting point of 239° to 241° C. and a TLC value (silica and EtOH, coloration with I$_2$) of Rf=0.00 to 0.01. The filtrate was distilled under reduced pressure to 4.9 g of imidazole (the recovery ratio was 72%).

EXAMPLE 2

In 7 ml of water were dissolved 21.9 g (0.1 mole) of a crystal of 2-($\beta$-(2'-methylimidazolyl-1'))-ethyl-4,6-diamino-S-triazine and 2.2 g (0.008 mole) of Na$_2$S.9H$_2$O, and the aqueous solution was sufficiently mixed, and dried and solidified under reduced pressure to obtain a starting material. This operation was performed so that the polymerization inhibitor was uniformly stuck to the crystal of the imidazolyl-S-triazine compound., The starting material was charged in a Claisen flask having a side arm and an inner capacity of about 100 ml and the bottom portion of the flask was wrapped with a hood on an electric heater. Heating was carried out under a reduced pressure of 5 mmHg and the inner temperature of the flask was maintained at 240° C. for 1 hour. After natural cooling, the sublimation product adhering to the inner wall of the upper portion and side arm of the flask was collected, and 35 ml of water was added to the collected sublimation product and the mixture was stirred at room temperature for a while. The insoluble substance (crude VT) was collected by filtration and was recrystallized from 110 ml of water to obtain 11 g (the yield being 80%) of intended VT characterized by a melting point of 239° to 241° C. and a TLC value (silica and EtOH, coloration with $I_2$) of Rf=0.00 to 0.01. The filtrate was distilled under reduced pressure to recover 5.8 g of 2-methylimidazole having a melting point of 115° to 118° C. (the recovery ratio was 71%).

EXAMPLE 3

In 7 ml of water was dissolved 24.7 g (0.1 mole) of a crystal of 2-($\beta$-(2'-ethyl-4'(5')-methylimidazolyl-1'))-ethyl-4,6-diamino-S-triazine and 4.8 g (0.02 mole) of $Na_2S.9H_2O$, and the aqueous solution was sufficiently mixed, and dried and solidified under reduced pressure to obtain a starting material. The starting material was charged in a Claisen flask having a side arm and an inner capacity of about 100 ml. The bottom portion of the flask was wrapped with a hood on an electric heater and heating was carried out under a reduced pressure of 5 mmHg to maintain the inner temperature of the flask at 300° C. for 1 hour. After natural cooling, the distillation product adhering to the upper portion and side arm of the flask was collected and washed with 35 ml of methanol at room temperature, and the insoluble substance (crude VT) was recovered by filtration in an amount of 9.6 g (0.07 mole) (the yield being 70%). The melting point of the recovered insoluble substance was 235° to 240° C. The insoluble substance was recrystallized from water to obtain 8.9 g (0.065 mole) (the yield being 65%) of purified intended VT characterized by a melting point of 239° to 241° C. and a TLC value (silica and EtOH, coloration with $I_2$) of Rf-0.00 to 0.01. The filtrate was distilled under reduced pressure to recover 9.35 g of 2-methyl-4(5)-methylimidazole (0.085 mole, the yield being 85%).

EXAMPLE 4

In 12 ml of water was dissolved 34.8 g (0.1 mole) of a crystal of 2-($\beta$-(2'-methylimidazolyl-1'))-ethyl-4,6-diamino-S-triazine/isocyanuric acid adduct and 1.2 g (0.005 mole) of $Na_2S.9H_2O$, and the aqueous solution was sufficiently stirred, and dried and solidified under reduced pressure to obtain a starting material. The starting material was charged in a Claisen flask having a side arm and an inner capacity of about 100 ml, and the bottom portion of the flask was wrapped with a hood on an electric heater. Heating was carried out under a reduced pressure of 5 mmHg and the inner temperature of the flask was maintained at 240° C. for 1 hour. After natural cooling, the sublimation product adhering to the inner wall of the upper portion and side arm of the flask was collected. Then, 50 ml of a 0.2N NaOH aqueous solution was added to the collected sublimation product and the mixture was heated and stirred for a while. The insoluble (crude VT) was recovered by filtration and recrystallized from 100 ml of water to obtain 10.4 g (the yield being 76%) of intended VT characterized by a melting point of 239° to 241° C. and a TLC value (silica and EtOH, coloration with $I_2$) of Rf=0.00 to 0.01.

EXAMPLE 5

In 7 ml of water were dissolved 21.9 g (0.1 mole) of 2-($\beta$-(2'-methylimidazolyl-1'))-ethyl-4,6-diamino-S-triazine and 2.2 g (0.008 mole) of $Na_2S.9H_2O$, and the aqueous solution was sufficiently mixed, and dried and solidified under reduced pressure to form a starting material. The starting material and 25 g of alumina powder were charged in a Claisen flask having a side arm and an inner capacity of about 100 ml, and the bottom portion of the flask was wrapped with a hood on an electric heater. Heating was carried out under a reduced pressure of 5 mmHg and the inner temperature of the flask was maintained at 320° C. for 45 minutes. After natural cooling, the sublimation product adhering to the inner wall of the upper portion and side arm of the flask was collected, and 50 ml of 0.2N NaOH aqueous solution was added to the collected sublimation product and the mixture was heated and stirred for a while. The insoluble substance (curde VT) was recovered by filtration and recrystallized from 100 ml of water to obtain 10.7 g (the yield being 78%) of intended VT characterized by a melting point of 239° to 241° C. and a TLC value (silica and EtOH, coloration with $I_2$) of Rf=0.00 to 0.01. Incidentally, the recovery ratio of 2-methylimidazole was 82%.

We claim:

1. A process for the synthesis of 2-vinyl-4,6-diamino-S-triazine having the following structural formula:

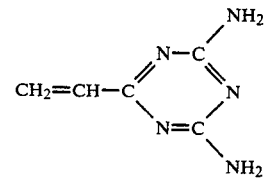

which comprises heating an imidazolyl-S-triazine compound represented by the following formula:

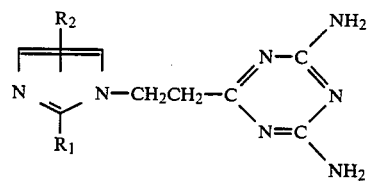

wherein $R_1$ stands for a hydrogen atom, a methyl group or an ethyl group, and $R_2$ stands for a hdyrogen atom or a methyl group, or an isocyanuric acid-addition product thereof under reduced pressure in the presence of a polymerization inhibitor.

2. A process according to claim 1, wherein the imidazolyl-S-triazine compound is 2-($\beta$-imidazolyl-(1'))-ethyl-4,6-diamino-S-triazine.

3. A process according to claim 1, wherein the imidazolyl-S-triazine compound is 2-($\beta$-(2'-methylimidazolyl-1'))-ethyl-4,6-diamino-S-triazine.

4. A process according to claim 1, wherein the imidazolyl-S-triazine compound is 2-($\beta$-(2'-ethyl-4'(5')-methylimidazolyl-1'))-ethyl-4,6-diamino-S-triazine.

5. A process according to claim 1, wherein the isocyanuric acid-addition product of the imidazolyl-S-triazine compound is used and is an isocyanuric acid-addition product of 2-($\beta$-(2'-methylimidazolyl-1'))-ethyl-4,6-diamino-S-triazine represented by the following formula:

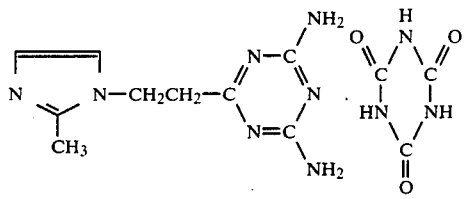

6. A process according to claim 1, wherein the polymerization inhibitor is sodium sulfide.

7. A process according to claim 1, wherein heating under reduced pressure is carried out in the co-presence of a powdery or granular heat-conducting medium.

8. A process according to claim 7, wherein the heat-conducting medium is quartz sand.

9. A process according to claim 7, wherein the heat-conducting medium is alumina powder.

10. The process according to claim 1 wherein the imidazolyl-S-triazine or its isocyanuric acid-addition product is heated at a temperature of 180° to 320° C. under a reduced pressure of about 5 to about 20 mmHg.

* * * * *